United States Patent [19]

Ishikawa et al.

[11] Patent Number: 4,540,698
[45] Date of Patent: Sep. 10, 1985

[54] 5-METHYLTHIOPYRIMIDINE DERIVATIVES, THEIR PREPARATION PROCESS AND FUNGICIDES CONTAINING SAME AS ACTIVE INGREDIENTS

[75] Inventors: Katsutoshi Ishikawa, Ashigara; Hitoshi Shimotori, Yokohama; Noboru Iida, Naga; Kazuo Akihiro, Yokohama; Shuji Ozawa, Zushi, all of Japan

[73] Assignee: Mitsui Toatsu Chemicals, Incorporated, Tokyo, Japan

[21] Appl. No.: 457,917

[22] Filed: Jan. 14, 1983

[30] Foreign Application Priority Data

Jan. 20, 1982 [JP] Japan ................................. 57-6142

[51] Int. Cl.$^3$ ................. A61K 31/515; C07D 239/62; C07D 239/66
[52] U.S. Cl. .................................. 514/270; 544/300; 544/301; 544/302
[58] Field of Search ................... 544/302, 300, 301; 424/251

[56] References Cited

U.S. PATENT DOCUMENTS 4,150,228  4/1979  Greenwald ................. 544/302
4,199,583  4/1980  Moon et al. ................. 424/251

OTHER PUBLICATIONS

Berichte der Deutschen Chemischen Gesellschaft, 36 2235, (1903).
Rodebush et al., J.A.C.S., 54(2), 731, (1932).
Maggiali et al., Ateneo Parmense, Act Nat. 1980, 16(3), pp. 117-125.
Maggiali et al., Chem. Abs., 95: 75433p, (1981).

Primary Examiner—Donald G. Daus
Assistant Examiner—Stephen M. Kapner
Attorney, Agent, or Firm—Fisher, Christen & Sabol

[57] ABSTRACT

Disclosed herein are a novel compound, 5-methylthiopyrimidine derivative, notably that represented by the following general formula:

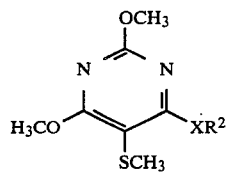

wherein X means an oxygen or sulfur atom and $R^2$ denotes a methyl, allyl or propargyl group, its preparation process and an agricultural and horticultural fungicide containing same as an active ingredient. The above compound exhibits outstanding control effects against plant diseases, especially, late blight of potatoes and the like and downly mildew. It permits preparation of an ideal agricultural and horticultural fungicide owing to its very low toxicity against mammal and fish and its no phytotoxicity.

6 Claims, 2 Drawing Figures

5-METHYLTHIOPYRIMIDINE DERIVATIVES, THEIR PREPARATION PROCESS AND FUNGICIDES CONTAINING SAME AS ACTIVE INGREDIENTS

TECHNICAL FIELD

This invention relates to novel 5-methylthiopyrimidine derivatives, their preparation process and fungicides containing same as active ingredients.

BACKGROUND ART

A huge number of studies, researches and investigations have heretofore been carried out on pyrimidine derivatives, leading to syntheses of a great number of compounds and finding of many compounds showing characteristic physiological activities in the fields of agricultural chemicals and pharmaceutical products. Many of these known pyrimidine derivatives were however prepared by substituting functional groups at the 2-, 4- and 6-positions of the pyrimidine skeltone, which functional groups are ready to undergo such substitution. The pyrimidine skeleton is much less reactive at its 5-position. There are only a few methods known to introduce a substituent group directly to the 5-position, all of which methods require to conduct nitration, halogenation or the like under certain specified conditions. Unless such known methods are followed, it is indispensable to employ an indirect method for the introduction of a desired substituent group, namely, to synthetically prepare a pyrimidine derivative from a compound which has in advance had the desired substituent group at a position corresponding to the 5-position of the resultant pyrimidine derivative.

As exemplary known pyrimidine derivatives having substituent groups at their 5-positions, may be mentioned as agricultural fungicides 5-n-butyl-2-dimethylamino-4-hydroxy-6-methylpyrimidine, 5-n-butyl-2-ethylamino-4-hydroxy-6-methylpyrimidine, etc. which are disclosed in British Patent Specification No. 1,182,584.

German Patent Offenlegungsschrift No. 2,341,925 discloses that the compounds represented by the general formula:

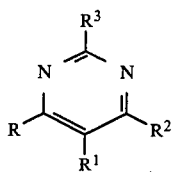

wherein $R^1$ is $-NO_2$, Me, Et, Cl, $-SCN$, $CO_2Et$, Br, $-CN$, $-SMe$, F, p$-ClC_6H_4S-$, BuO$-$ or $-CHO$ and $R^2$ means a morpholino or piperidino group are useful as pharmaceutical products.

There are a relatively small number of compounds having a methylthio group as a substituent group attached to the 5-position. Except for the compounds described in the above-referred to specifications, there have been known only the following related compounds which are all disclosed in the Chemical Abstracts:

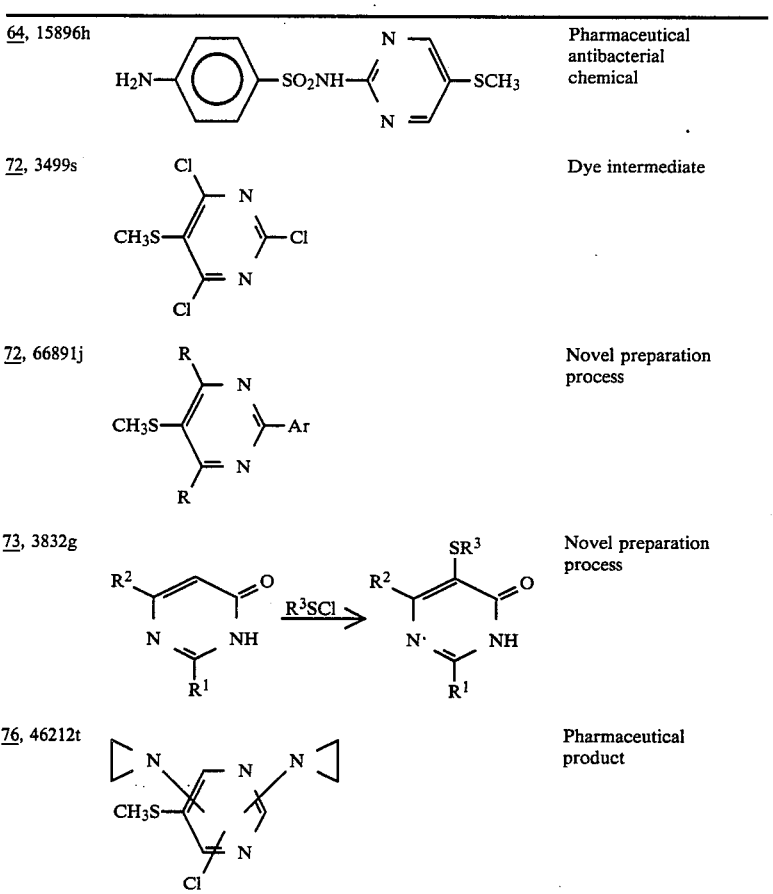

| | | |
|---|---|---|
| 78, 97696c | 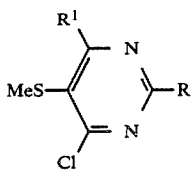 | R, R¹: amino groups; herbicide; fungicide |
| 79, 137181k | 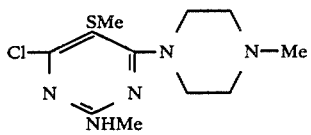 | Pharmaceutical product |
| 82, 156364f | 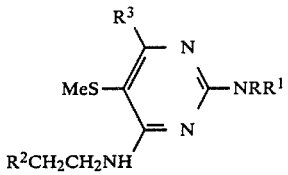 | Pharmaceutical product |
| 89, 101721d | 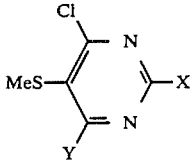 | X,Y: Cl, alkylamino; herbicide |
| 90, 54968y | 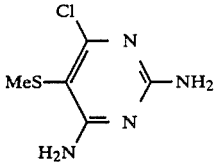 | Herbicide |

As illustrated above, substituent groups are bonded in many instances to the pyrimidine rings through nitrogen atoms in the above known 5-methylthiopyrimidine derivatives having substituent groups at their 2-, 4- and 6-positions. There have not been known to date any compounds which have, at all the 2-, 4- and 6-positions thereof, substituent groups bonded to the pyrimidine rings through oxygen or sulfur atoms.

The present inventors have synthetically obtained compounds having the above-mentioned structure, which compounds have never been synthesized so far, and tested their physiological effects, resulting in completion of this invention.

DISCLOSURE OF THE INVENTION

One object of this invention is to provide a novel 5-methylthiopyrimidine derivative.

Another object of this invention is to provide a preparation process for obtaining the 5-methylthiopyrimidine derivative.

A further object of this invention is to provide a novel agricultural and horticultural fungicide, especially, a novel chemical composition capable of exhibiting outstanding control effects against late blight and downy mildew.

All the above objects have been respectively achieved by the provision of:

A 5-methylthiopyrimidine derivative represented by the following general formula (I):

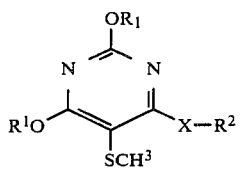

wherein $R^1$ means an alkyl group having 1-6 carbon atoms or a phenyl, benzyl, alkenyl or alkoxyalkyl group, $R^2$ denotes an alkyl group having 1-6 carbon atoms, a phenyl, halogensubstituted phenyl, alkenyl, ω-phenyl-substituted alkenyl, alkynyl, alkoxyalkyl, alkoxyalkoxyalkyl, alkylthioalkyl, aminoalkyl, alkoxycarbonylalkyl, aminocarbonylalkyl, furfuryl, thienylmethyl or tetrahydrofuryl group or a

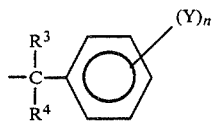

in which $R^3$ and $R^4$ are individually a hydrogen atom or methyl group, Y means a hydrogen or halogen atom or a methyl or methoxy group, and n stands for an integer of 1 or 2, and X denotes an oxygen or sulfur atom;

A process for preparing a 5-methylthiopyrimidine derivative represented by the above-defined general formula (I), which process comprises the following consecutive steps:

reacting, in the presence of a base and at a temperature below room temperature, 5-methylthio-2,4,6-trichloropyrimidine with two equivalents of a compound represented by the following general formula (IV):

R₁OH   (IV)

wherein R¹ has the same significance as defined above in the general formula (I) so as to form a dialkoxypyrimidine derivative represented by the following general formula (III):

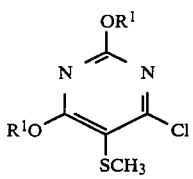

(III)

wherein R¹ has the same significance as defined above in the general formula (I); and reacting, in the presence of a base, the dialkoxypyrimidine derivative with a compound represented by the following general formula (II):

R²XH   (II)

wherein R² has the same significance as defined above in the general formula (I);

A process for preparing 5-methylthiopyrimidine derivative represented by the above-defined general formula (I), which process comprises the following consecutive steps:

reacting, in the presence of a base and at a temperature below room temperature, 5-methylthio-2,4,6-trichloropyrimidine with an equivalent of a compound represented by the following general formula (II):

R²XH   (II)

where R² and X have the same significance as defined above in the general formula (I) so as to form a monosubstituted derivative represented by the following general formula (V):

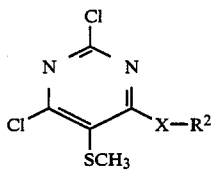

(V)

wherein R² and X have the same significance as defined above in the general formula (I); and reacting, in the presence of a base, the monosubstituted derivative with a compound represented by the following general formula (IV):

R¹OH   (IV)

wherein R¹ has the same significance as defined above in the general formula (I); and An agricultural and horticultural fungicide comprising, as an active ingredient thereof, a 5-methylthiopyrimidine derivative represented by the above-defined general formula (I).

The compounds according to this invention pertain to excellent fungicidal activities and multiplication inhibitory effects against plant pathogens and can thus be applied to control plant diseases developed by a wide variety of pathogens.

The compounds according to this invention exhibit outstanding control effects against potato late blight (*Phytophthora infestans*), tomato late blight (*Phytophthora infestans*), black shank (*Phytophthora parasitica var. nicotiana*), grape downy mildew (*Plasmopara viticola*), cucumber downy mildew (*Pseudoperonospora cubensis*), etc., namely, plant diseases developed by so-called phycomycetes, alternaria leaf spot (*Alternaria mali*), grey mold (*Botrytis cinerea*), and the like.

Furthermore, the compounds according to this invention do no practically show any phytotoxicity against cultivated plants. Their toxicity are extremely low against warm-blooded animals such as, for example, mice, rats, dogs and poultry and they do not show any toxicity at all against fish. Therefore, they paettain to extremely good properties as agricultural fungicides.

BEST MODE OF CARRYING OUT THE INVENTION

Figure 1:
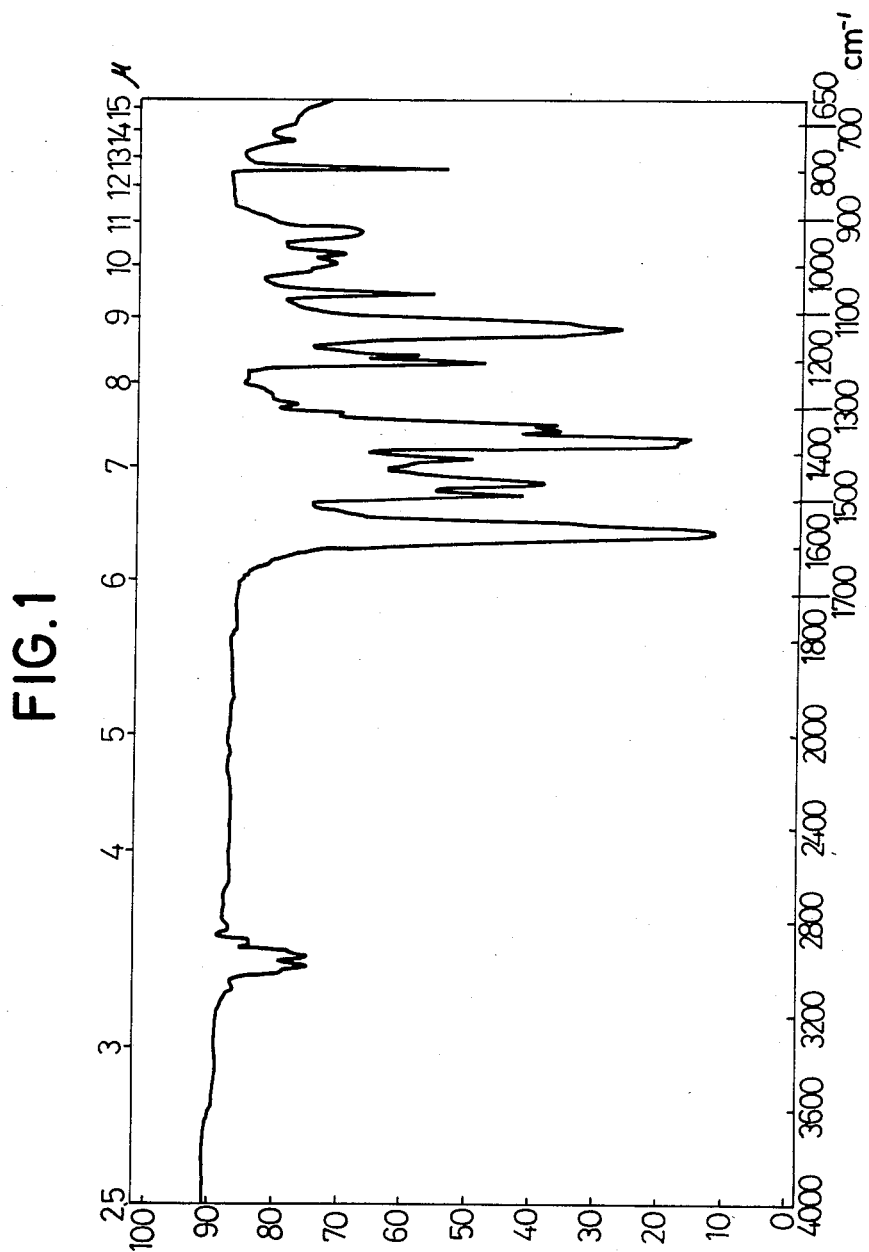
FIGS. 1 and 2 show infrared absorption spectra of Compound Nos. 8 and 45, respectively.

The compounds of this invention may be prepared following the below-described route (a) or route (b).

5-Methylthio-2,4,6-trichloropyrimidine, the starting material, may be prepared in accordance with the method described in the Chemical Abstracts, 72, 3499s. Parts of the preparation method, which parts pertain to the present invention, will next be described from one preparation step to another by means of reaction equations.

Route (a):

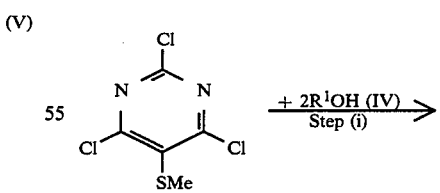

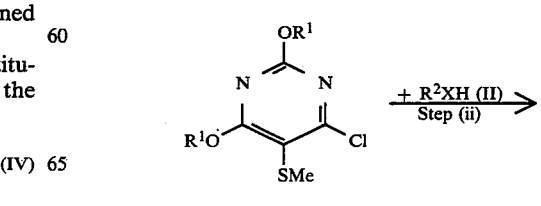

(III)

-continued

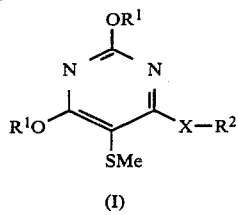

(I)

Step (i): It is possible to use, as a solvent, a solvent inert to alkali metals such as tetrahydrofuran, dioxane, N,N-dimethylformamide, 1,3-dimethyl-2-imidazolidinone, dimethylsulfoxide, hexamethylphosphoramide, benzene, toluene or an ether or the alcohol $R^1OH$ per se. Two equivalents or slightly excess $R^1OH$ are diluted in the solvent ($R^1OH$ is used in a larger volume when it is used also as a solvent), followed by an addition of two equivalents or slightly excess alkali metal, sodium hydride or potassium hydride. Upon thoroughly stirring the resultant mixture, an alcoholate is formed. The reaction system may be heated to the boiling point of the solvent if the reaction is slow. After preparation of the alcoholate, 5-methylthio-2,4,6-trichloropyrimidine is added little by little in its inherent solid form or as a solution dissolved in a solvent. The reaction temperature may range from $-10°$ C. to the boiling point of the solvent. The compound (III) is obtained with good selectivity when 5-methylthio-2,4,6-trichloropyrimidine is added at a temperature below room temperature.

In some instances, an alkali metal hydroxide or its analogous compound may be used in lieu of an alkali metal or sodium hydride. This technique is advantageous where $R^1$ stands for an alkyl group having 1-3 carbon atoms. Namely, a predetermined amount of an alkali metal hydroxide is added into a suitable amount of an alcohol which serves also as a solvent and 5-methylthio-2,4,6-trichloropyrimidine is then added in its inherent solid form or as a solution dissolved in an appropriate solvent. The alkali metal hydroxide may be added at the very end. The alkali metal hydroxide may be added as either solid or aqueous solution. The term "base" as used herein thus embraces alkali metals, sodium hydride, potassium hydride and alkali metal hydroxides. It is not essential in the above reaction that $R^1OH$ beforehand forms an alcoholate with a base.

The compound (III) can be readily isolated but the reaction mixture may be passed to the following step (ii) without isolating the compound (III) therefrom. Where $R^1$ and $R^2$ represent the same group and X denotes an oxygen atom, it is possible to obtain the compound (I) directly using $R^1OH$ and the base, each, in an amount of 3 equivalents or more from the beginning.

Step (ii): It is feasible to use the same solvent and base as used in the step (i). Similar to the step (i), the reaction may be carried out using an alcoholate or thiolate which has been prepared in advance. Furthermore, an aqueous solution of an alkali metal hydroxide may be used as a base as is. The reaction may be effected by either dropping a solution containing an equivalent or slightly excess $R^2XH$ and base little by little into a solution of the compound (III) or, on the contrary, adding the compound (III) in its inherent form or as a solution dissolved in a suitable solvent into a solution containing $R^2XH$ and base. Although the reaction temperature may range from $0°$ C. to the boiling point of a solvent to be employed, the reaction may in many instances be brought to completion at room temperature. The reaction is, in many cases, completed in 2-3 hours. The compound (I) can be purified in accordance with recrystallization, distillation under reduced pressures or column chromatography.

Route (b):

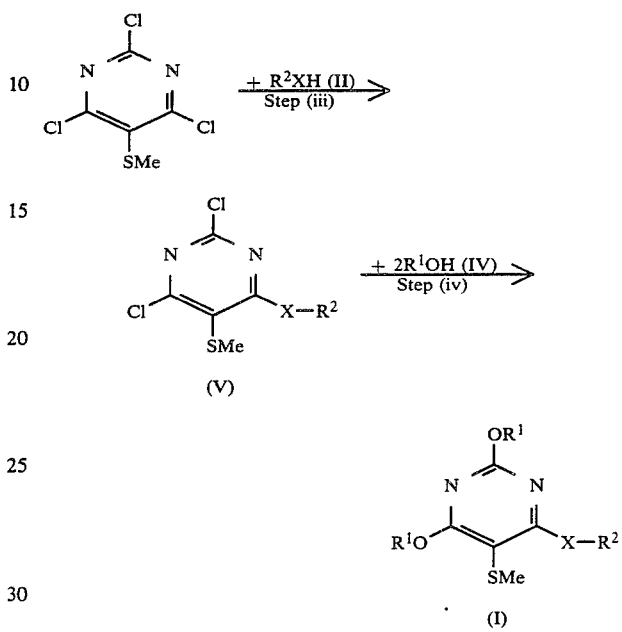

Step (iii): The same solvent and base as those employed in the step (ii) may be used. The reaction is effected by either adding dropwise and little by little a solution containing the equivalent or slightly excess $R^2XH$ and base, which solution has in advance been prepared, into a solution of 5-methylthio-2,4,6-trichloropyrimidine or, on the contrary, adding 5-methylthio-2,4,6-trichloropyrimidine in its inherent solid form or as a solution dissolved in a solvent into a solution containing $R^2XH$ and base. The reaction temperature may range from $-10°$ C. to the boiling point of a solvent to be used but it is desirous to carry out the reaction at temperatures as low as feasible because such low temperatures are effective to avoid occurrence of side reactions which lead to the formation of multi-substituted derivatives. Preferred reaction temperature may range from $0°$ C. to room temperature. The reaction is completed mostly in 1-3 hours.

Step (iv): The reaction may be carried out using the same solvent and base as used in the step (i). Namely, when following the method of forming an alcoholate in advance, two equivalents or slightly excess $R^1OH$ is diluted in a solvent ($R^1OH$ is used in a larger volume when it is used, also, as a solvent). The thus-prepared solution is then added with two equivalents or slightly excess of an alkali-metallizing agent such as an alkali metal or sodium hydride, followed by thorough agitation of the resultant mixture to form an alcoholate. The reaction system may be heated to the boiling point of the solvent if the reaction is slow. Subsequent to formation of the alcoholate, the compound (V) is added little by little in its inherent solid form or as a solution dissolved in a solvent. The reaction temperature may range from $0°$ C. to the boiling point of a solvent to be used but it is desirous to effect the reaction at room temperature. The reaction can, in many instances, be brought to completion in 1-5 hours. Similar to the step (i), an alkali metal hydroxide or its analogous compound may be used in place of an alkali metal or sodium hydride if desired or needed.

The thus-prepared compound (I) may be purified in the same manner as in the step (ii).

Preparation processes of the compounds according to this invention will hereinafter be described specifically with reference to the following Synthesis Examples:

Synthesis Example 1:

Synthesis of
2,4-dimethoxy-5,6-bis(methylthio)pyrimidine
(Compound No. 1) . . . Route (a)

(1) Synthesis of 6-chloro-2,4-dimethoxy-5-methylthiopyrimidine:

Subsequent to charging 30 ml of dry methanol into a 50-milliliter, 4-necked flask equipped with a reflux condenser provided with a tubular calcium chloride trap, thermometer and stirrer, 0.37 g of metallic sodium was added as small pieces. After dissolving metallic sodium, 1.84 g of 5-methylthio-2,4,6-trichloropyrimidine was added little by little at 0° C. The reaction mixture was stirred for 15 minutes at 0° C. and then for further 15 minutes at room temperature. The resultant liquid reaction mixture was poured into ice water. The thus-formed solid precipitate was then collected by filtration and recrystallized from n-hexane, thereby obtaining 6-chloro-2,4-dimethoxy-5-methylthiopyrimidine (m.p. 58.5°-59.5° C.). Yield: 1.40 g (79.1%).

NMR(CCl$_4$)δ: 2.30(3H, s), 3.97(3H, s), 4.04(3H, s)

(2) Synthesis of 2,4-dimethoxy-5,6-bis(methylthio)pyrimidine:

Into a 100-milliliter, 4-necked flask equipped with a reflux condenser, thermometer and stirrer, were charged 5.51 g of 6-chloro-2,4-dimethoxy-5-methylthiopyrimidine and 50 ml of tetrahydrofuran. After causing the pyrimidine derivative to dissolve completely in the solvent, a 15% aqueous solution of sodium methyl mercaptan (commercially available; product of Tokyo Kasei Kogyo K.K.) was added dropwise and the resultant mixture was refluxed for 5 hours.

The liquid reaction mixture was poured into ice water, followed by its extraction with ethyl acetate. The ethyl acetate layer was washed with water and dried with anhydrous sodium sulfate. Then, the solvent was driven off and the resultant crude reaction product was recrystallized from n-hexane, thereby obtaining 2,4-dimethoxy-5,6-bis(methylthio)pyrimidine (m.p. 60°-61° C.). Yield: 4.76 g (82.1%).

NMR(CCl$_4$)δ: 2.21(3H, s), 2.46(3H, s), 3.97(3H, s), 4.02(3H, s)

Synthesis Example 2:

Synthesis of 5-methylthio-2,4,6-trimethoxypyrimidine
(Compound No. 2) . . . Route (a)

Charged into a 100-milliliter, 4-necked flask equipped with a reflux condenser provided with a tubular calcium chloride trap, thermometer and stirrer was 60 ml of dry methanol. Thereafter, 3.45 g of metallic sodium was added as small pieces and dissolved completely, followed by an addition of 5.74 g of 5-methylthio-2,4,6-trichloropyrimidine at room temperature. The reaction mixture was then heated gradually and refluxed for 30 minutes. The liquid reaction mixture was poured into ice water and the resulting solid precipitate was collected by filtration and dried, leading to the provision of 4.61 g of 5-methylthio-2,4,6-trimethoxypyrimidine as crude crystals (Yield: 85%). A TLC analysis found that the crude crystals consisted substantially of the above single compound. Their recrystallization from a mixed solvent of n-hexane and benzene gave the reaction product in a purified form (m.p. 90.5°-91° C.).

NMR(CDCl$_3$)δ: 2.25(3H, s), 3.98(3H, s), 4.03(6H, s)

Synthesis Example 3:

Synthesis of
6-t-butoxy-2,4-dimethoxy-5-methylthiopyrimidine
(Compound No. 3) . . . Route (b)

Into a 50-milliliter, 4-necked flask equipped with a reflux condenser provided with a tubular calcium chloride trap, thermometer and stirrer, were charged 20 ml of tetrahydrofuran and 0.8 g of t-butanol. Thereafter, 0.44 g of sodium hydride (content: 60%) was incorporated. The thus-prepared mixture was stirred at room temperature, followed by an addition of 5 ml of hexamethylphosphoramide and a subsequent dropwise addition at room temperature of a solution prepared by dissolving 1.03 g of 5-methylthio-2,4,6-trichloropyrimidine in 10 ml of tetrahydrofuran. After agitating the resultant mixture at room temperature for 30 minutes, was dropped a tetrahydrofuran solution of sodium methylate (containing 1.0 g in terms of sodium methylate) which had been prepared on the side. The thus-formed mixture was stirred for further 30 minutes at room temperature.

The liquid reaction mixture was then poured into water and extracted with n-hexane. The n-hexane layer was washed with water and, subsequent to its drying, the solvent was driven off by distillation to give a crude reaction product. It was then purified by column chromatography (adsorbent: silica gel; solvent: a 100:6 mixture of n-hexane and ethyl acetate), thereby obtaining 0.70 g of 6-t-butoxy-2,4-dimethoxy-5-methylthiopyrimidine as an oily substance (yield: 60.3%).

NMR(CCl$_4$)δ: 1.64(9H, s), 2.16(3H, s), 3.87(3H, s), 3.95(3H, s)

Synthesis Example 4:

Synthesis of 5-methylthio-2,4,6-trimethoxypyrimidine
(Compound No. 2)

Into a 50-milliliter, 4-necked flask equipped with a reflux condenser, thermometer and stirrer, were charged 1.4 g of granular sodium hydroxide (purity: 95%) and 20 ml of methanol. The contents of the flask were thoroughly agitated to dissolve the former in the latter, followed by a dropwise addition of a solution which had been prepared by dissolving 2.3 g of 5-methylthio-2,4,6-trichloropyrimidine in 10 ml of tetrahydrofuran. The above dropwise addition was accompanied by producton of heat and the temperature of the reaction mixture rose from room temperature (20° C.) to 35° C. The reaction mixture was heated and refluxed with stirring for two hours. After cooling, the liquid reaction mixture was poured into water and the resultant crystalline deposit was collected by filtration. It was then thoroughly washed with water. It was dried under reduced pressure, thereby obtaining 5-methylthio-2,4,6-trimethoxypyrimidine (m.p. 90°-91° C.). It gave a single spot by silica gel thin-layer chromatography (development solvent: n-hexane/ethyl acetate=7/3). Yield: 1.91 g(88.4%).

Synthesis Example 5:

Synthesis of 5-methylthio-2,4,6-trimethoxypyrimidine (Compound No. 2)

Charged into a 100-milliliter, 4-necked flask equipped with a reflux condenser, thermometer and stirrer were 2.2 g of 6-chloro-2,4-dimethoxy-5-methylthiopyrimidine and 40 ml of methanol. They were stirred into a homogeneous solution. Subsequent to an addition of 2.0 g of potassium hydroxide, the resultant mixture was heated and refluxed, with thorough stirring, for 3 hours. The liquid reaction mixture was then poured into water and the resultant solid precipitate was collected by filtration. It was recrystallized from isopropyl alcohol, thereby obtaining 5-methylthio-2,4,6-trimethoxypyrimidine (m.p. 90°–91° C.). Yield: 1.96 g (90.7%).

Figure 2:
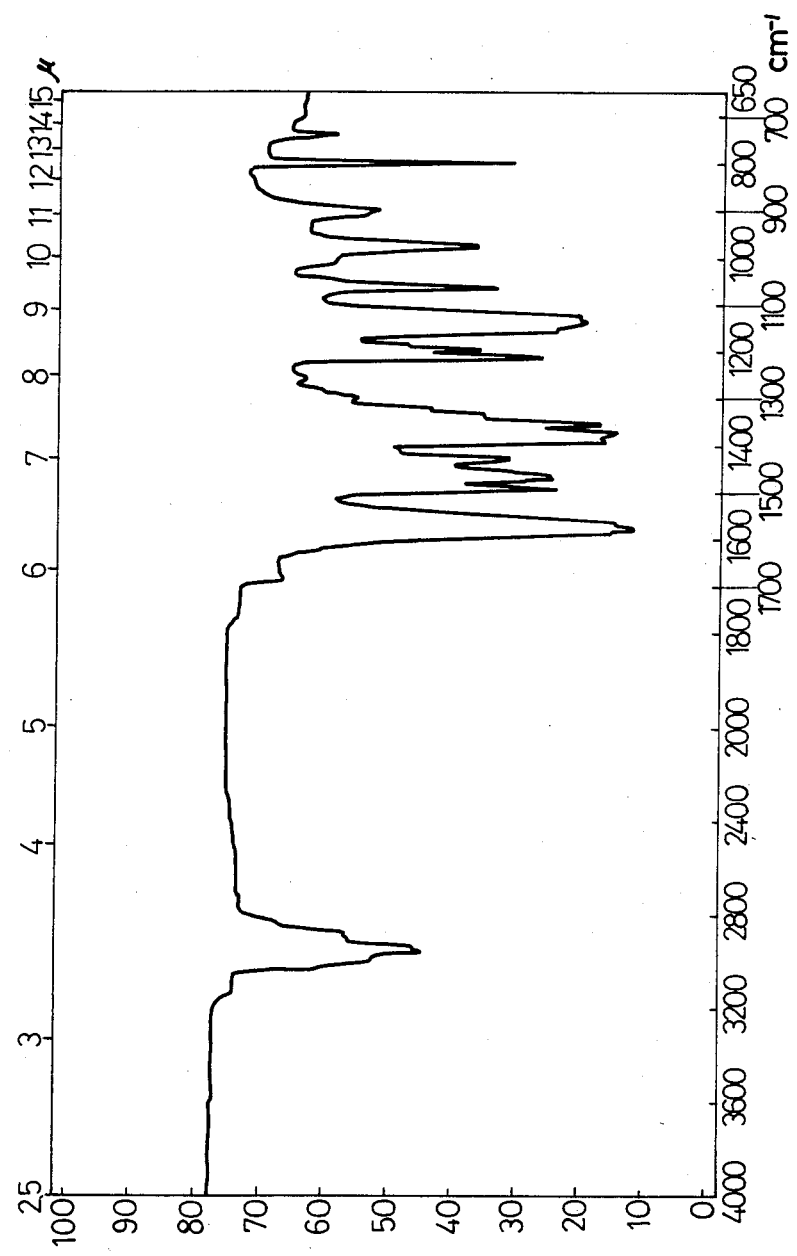

The compounds according to this invention, which represented by the general formula (I), can all be synthesized practically following the above Synthesis Examples. Certain representative examples of the 5-methylthiopyrimidine derivatives according to this invention which examples were prepared in accordance with the above process, their synthesis routes and melting points, and their physical data such as NMR data and the like are shown in Table 1. Among the above examples, Compound Nos. 8 and 45 were subjected to infrared absorption spectrography and resultant infrared absorption spectra are shown respectively in FIGS. 1 and 2. The measurement of the infrared absorption spectra was conducted using an IRA-1 spectrometer of Nippon Bunko K.K. and following the neat method.

TABLE 1

| Compound No. | $R^1$ | X | $R^2$ | Synthesis route | Physical data m.p. and/or NMR(100MHz, δ) |
|---|---|---|---|---|---|
| 4 | Et | O | Et | (a) | Oily substance NMR(CCl$_4$): 1.36(3H, t, J = 6.8Hz), 1.40(6H, t, J = 6.8Hz), 2.15(3H, s), 4.23(2H, q, J = 6.8Hz), 4.36 (4H, q, J = 6.8Hz) |
| 5 | n-propyl | O | n-propyl | (a) | Oily substance NMR(CCl$_4$): 1.07(9H, t, J = 7.6Hz), 1.6–2.0(6H, m), 2.19(3H, s), 4.17(2H, t, J = 6.6Hz), 4.29(4H, t, J = 6.6Hz) |
| 6 | i-propyl | O | i-propyl | (a) | Oily substance NMR(CCl$_4$): 1.36(6H, d, J = 6.0Hz), 1.39(12H, d, J = 6.0Hz), 2.17 (3H, s), 5.09(1H, q, J = 6.0Hz), 5.33(2H, q, J = 6.0Hz) |
| 7 | n-butyl | O | n-butyl | (a) | Oily substance NMR(CCl$_4$): 1.00(9H, t, J = 7.4Hz), 1.3–1.9(12H, m), 2.18(3H, s), 4.20(2H, t, J = 6.0Hz), 4.32(4H, t, J = 6.0Hz) |
| 8 | Me | O | —CH$_2$—CH=CH$_2$ | (a) | Oily substance NMR(CCl$_4$): 2.18(3H, s), 3.88(3H, s), 3.96(3H, s), 4.7–4.9(2H, m), 5.1–5.5(2H, m), 5.8–6.2(1H, m) |
| 9 | —CH$_2$—CH=CH$_2$ | O | Me | (b) | Oily substance NMR(CCl$_4$): 2.18(3H, s), 3.96(3H, s), 4.7–4.9(4H, m), 5.1–5.5(4H, m), 5.8–6.2(2H, m) |
| 10 | —CH$_2$—CH=CH$_2$ | O | —CH$_2$—CH=CH$_2$ | (a) | Oily substance NMR(CCl$_4$): 2.21(3H, s), 4.7–4.9 (6H, m), 5.1–5.5(6H, m), 5.8–6.2 (3H, m) |
| 11 | Me | S | —CH$_2$COOEt | (a) | m.p. 78–79° C. NMR(CCl$_4$): 1.26(3H, t, J = 7Hz), 2.23(3H, s), 3.90(3H, s), 3.98 (3H, s), 4.12(2H, q, J = 7Hz) |
| 12 | Me | O | —CH$_2$CH$_2$OCH$_3$ | (a) | Oily substance NMR(CCl$_4$): 2.17(3H, s), 3.36(3H, s), 3.65(2H, t, J = 5Hz), 3.86(3H, s), 3.94(3H, s), 4.44(2H, t, J = 5Hz) |
| 13 | —CH$_2$CH$_2$OCH$_3$ | O | Me | (b) | Oily substance NMR(CCl$_4$): 2.17(3H, s), 3.36(6H, s), 3.55–3.80(4H, m), 3.95(3H, s), 4.25–4.56(4H, m) |
| 14 | Me | O | —(CH$_2$CH$_2$O)$_2$CH$_3$ | (a) | Oily substance NMR(CCl$_4$): 2.18(3H, s), 3.28(3H, s), 3.34–3.70(4H, m), 3.70–4.10 (8H, m), 4.27–4.58(2H, m) |
| 15 | Me | O | —CH$_2$—(furyl) | (a) | Oily substance NMR(CCl$_4$): 2.12(3H, s), 3.88(3H, s), 3.93(3H, s), 5.32(2H, s), 6.2–6.5(2H, m), 7.35(1H, broad) |
| 16 | Me | O | —CH$_2$—C≡CH | (a) | m.p. 54–55° C. NMR(CCl$_4$): 2.20(3H, s), 2.40(1H, t, J = 2Hz), 3.90(3H, s), 3.97(3H, s), 4.97(2H, d, J = 2Hz) |

TABLE 1-continued

| Compound No. | R¹ | X | R² | Synthesis route | Physical data m.p. and/or NMR(100MHz, δ) |
|---|---|---|---|---|---|
| 17 | Me | O | —CH₂—C₆H₅ | (a) | Soft solid substance NMR(CCl₄): 2.17(3H, s), 3.87(3H, s), 3.96(3H, s), 5.40(2H, s), 7.0–7.5(5H, m) |
| 18 | —CH₂—C₆H₅ | O | Me | (b) | Oily substance NMR(CCl₄): 2.17(3H, s), 3.95(3H, s), 5.27(2H, s), 5.38(2H, s), 7.07–7.5(10H, m) |
| 19 | Me | O | —CH₂CH₂NH₂ | (a) | Oily substance NMR(CCl₄): 1.44(2H, broad), 2.20 (3H, s), 3.01(2H, t, J = 6Hz), 3.90 (3H, s), 4.00(3H, s), 4.35(2H, t, J = 6Hz) |
| 20 | Et | O | Me | (b) | Oily substance NMR(CCl₄): 1.15–1.60(6H, m), 2.20 (3H, s), 3.99(3H, s), 4.18–4.60 (4H, m) |
| 21 | Me | S | Et | (a) | m.p. 32–34° C. NMR(CCl₄): 1.36(3H, t, J = 7Hz), 2.19(3H, s), 3.05(2H, q, J = 7Hz), 3.93(3H, s), 3.98(3H, s) |
| 22 | Me | S | i-propyl | (a) | m.p. 43–45° C. NMR(CCl₄): 1.41(6H, d, J = 7Hz), 2.18(3H, s), 3.60–4.10(1H, m), 3.93(3H, s), 3.99(3H, s) |
| 23 | Me | S | —CH₂CH₂NH₂ | (a) | Oily substance NMR(CDCl₃): 1.85(2H, broad), 2.28 (3H, s), 2.82(2H, broad), 3.25(2H, broad), 4.00(3H, s), 4.04(3H, s) |
| 24 | Me | O | Et | (a) | Oily substance NMR(CCl₄): 1.23(3H, t, J = 7Hz), 2.17(3H, s), 3.89(3H, s), 3.97(3H, s) 4.22(2H, q, J = 7Hz) |
| 25 | Me | O | i-propyl | (a) | Oily substance NMR(CCl₄): 1.37(3H, d, J = 6Hz), 1.39(3H, d, J = 6Hz), 2.17(3H, s), 3.89(3H, s), 3.97(3H, s), 5.28(1H, m) |
| 26 | Me | O | —CH₂—C(=O)—N(CH₂—CH=CH₂)₂ | (a) | m.p. 87–88.5° C. NMR(CCl₄): 2.35(3H, s), 3.6–4.2 (10H, m), 4.8–5.5(6H, m), 5.5–6.1 (2H, m) |
| 27 | C₆H₅ | O | C₆H₅ | (a) | m.p. 128–128.5° C. NMR(CCl₄): 2.46(3H, s), 6.8–7.4 (15H, m) |
| 28 | Me | O | tetrahydrofuranyl | (a) | Oily substance NMR(CCl₄): 2.02–2.36(5H, m), 3.60–4.20(10H, m), 5.50(1H, m) |
| 29 | Me | O | —CH₂—CH=CH—C₆H₅ | (a) | Oily substance NMR(CCl₄): 2.22(3H, s), 3.92(3H, s), 4.00(3H, s), 5.04(2H, d, J = 7Hz), 6.40(1H, double t, J = 7Hz, 16Hz), 3.75(1H, d, J = 16Hz), 7.0–7.5(5H, m) |
| 30 | Me | O | —CH₂—C₆H₄—Cl | (a) | m.p. 85–87° C. NMR(CCl₄): 2.16(3H, s), 3.90(3H, s), 3.99(3H, s), 5.38(2H, s), 7.26(2H, d, J = 8Hz), 7.4(2H, d, J = 8Hz) |
| 31 | Me | O | —CH₂—C₆H₄(Cl) | (a) | m.p. 100–102° C. NMR(CCl₄): 2.18(3H, s), 3.84(3H, s), 3.94(3H, s), 5.28(2H, s), 7.1–7.7(4H, m) |

TABLE 1-continued

| Compound No. | Substituent groups in the general formula (I) | | | Synthesis route | Physical data m.p. and/or NMR(100MHz, δ) |
|---|---|---|---|---|---|
| | R¹ | X | R² | | |
| 32 | Me | O | −CH₂−C₆H₄−Cl (4-Cl) 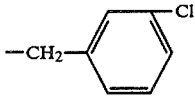 | (a) | m.p. 57–59° C.<br>NMR(CCl₄): 2.18(3H, s), 3.86(3H, s), 3.95(3H, s), 5.36(2H, s), 7.16–7.50(4H, m) |
| 33 | Me | O | −CH₂−C₆H₃−Cl₂ (2,4-Cl₂) 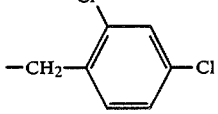 | (a) | m.p. 118–120° C.<br>NMR(CCl₄): 2.20(3H, s), 3.87(3H, s), 3.96(3H, s), 5.24(2H, s), 7.2–7.6(3H, m) |
| 34 | Me | O | −CH₂−C₆H₃−Cl₂ (2,5-Cl₂) 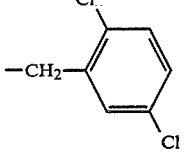 | (a) | m.p. 111–112° C.<br>NMR(CCl₄): 2.22(3H, s), 3.88(3H, s), 3.98(3H, s), 5.44(2H, s), 7.16–7.60(3H, m) |
| 35 | Me | O | −CH₂−C₆H₃−Cl₂ (2,3-Cl₂) 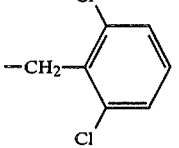 | (a) | m.p. 135–136° C.<br>NMR(CCl₄): 2.10(3H, s), 3.92(3H, s), 3.96(3H, s), 5.58(2H, s), 7.10–7.44(3H, m) |
| 36 | Me | O | −CH₂−C₆H₃−Cl₂ (3,4-Cl₂) 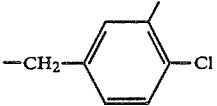 | (a) | m.p. 111–112.5° C.<br>NMR(CCl₄): 2.16(3H, s), 3.85(3H, s), 3.96(3H, s), 5.32(2H, s), 7.10–7.54(3H, m) |
| 37 | Me | O | −CH₂−C₆H₃−Cl₂ (3,5-Cl₂) 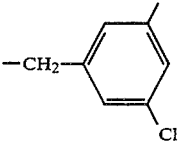 | (a) | m.p. 90–93° C.<br>NMR(CCl₄): 2.20(3H, s), 3.86(3H, s), 3.96(3H, s), 5.32(2H, s), 7.16–7.32(3H, m) |
| 38 | Me | O | −CH₂−C₆H₄−OCH₃ 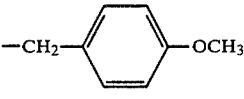 | (a) | Oily substance<br>NMR(CCl₄): 2.16(3H, s), 3.74(3H, s), 3.87(3H, s), 3.94(3H, s), 5.32(2H, s), 6.7–7.4(4H, m) |
| 39 | Me | S | −CH₂−C₆H₅ 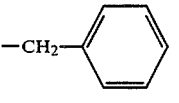 | (a) | Oily substance<br>NMR(CCl₄): 2.14(3H, s), 3.88(3H, s), 3.94(3H, s), 4.27(2H, s), 7.1–7.2(5H, m) |
| 40 | Me | O | −CH₂−(2-thienyl) 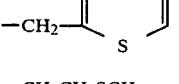 | (a) | Oily substance<br>NMR(CCl₄): 2.16(3H, s), 3.94(3H, s), 3.97(3H, s), 5.56(2H, s), 6.8–7.3(3H, m) |
| 41 | Me | O | −CH₂CH₂SCH₃ | (a) | Oily substance<br>NMR(CCl₄): 2.20(3H, s), 2.23(3H, s), 2.83(2H, t, J = 7Hz), 3.91(3H, s), 3.99(3H, s), 4.52(2H, t, J = 7Hz) |
| 42 | Me | O | −C₆H₄−Cl (4-Cl) 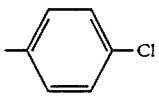 | (a) | Oily substance<br>NMR(CCl₄): 2.28(3H, s), 3.72(3H, s), 4.02(3H, s), 7.06(2H, d, J = 9.2Hz), 7.31(2H, d, J = 9.2Hz) |

TABLE 1-continued

| Compound No. | Substituent groups in the general formula (I) | | | Synthesis route | Physical data m.p. and/or NMR(100MHz, δ) |
|---|---|---|---|---|---|
| | $R^1$ | X | $R^2$ | | |
| 43 | Me | O | —⟨C$_6$H$_4$⟩—F | (a) | Oily substance<br>NMR(CCl$_4$): 2.31(3H, s), 3.72(3H, s), 4.04(3H, s), 7.0–7.2(4H, m) |
| 44 | Me | O | —CH$_2$—C(CH$_3$)=CH$_2$ | (a) | Oily substance<br>NMR(CCl$_4$): 1.84(3H, s), 2.19(3H, s), 3.88(3H, s), 3.97(3H, s), 4.75(2H, s), 4.90(1H, s), 5.06(1H, s) |
| 45 | Me | O | —CH$_2$—CH=CH—CH$_3$ | (a) | Oily substance<br>NMR(CCl$_4$): 1.78(3H, d, J = 4.4Hz), 2.20(3H, s), 3.94(3H, s), 4.02(3H, s), 4.84(2H, d, J = 4.8Hz), 5.6–5.9(2H, m) |
| 46 | Me | O | —CH(CH$_3$)—C$_6$H$_5$ | (a) | Oily substance<br>NMR(CCl$_4$): 1.67(3H, d, J = 6.8Hz), 2.20(3H, s), 3.79(3H, s), 3.92(3H, s), 6.16(1H, q, J = 6.8Hz), 7.1–7.5(5H, m) |

Note:
In the NMR data, s, d, t, q and m mean respectively singlet, doublet, triplet, qualtet and multiplet.

Although the compound according to this invention may be used as agricultural and horticultural fungicides without any additives thereto, they are actually mixed with a carrier and, if necessary, other adjuvants and processed for their application into preparation forms commonly employed as agricultural and horticultural fungicides such as, for example, dust(concentration of active ingredient: 1–10%), coarse dust(concentration of active ingredient: 1–10%), micro-granules(concentration of active ingredient: 1–25%), granules(concentration of active ingredient: 2–30%), wettable powder(concentration of active ingredient: 20–80%), emulsifiable concentrate(concentration of active ingredient: 10–50%), oil suspension(concentration of active ingredient: 10–70%), oil solution(concentration of active ingredient: 10–50%), smoking chemicals(concentration of active ingredient: 2–70%), fumigants(concentration of active ingredient: 2–70%), microcapsules(concentration of active ingredient: 10–80%) and the like.

By the term "carrier" as used herein is meant a synthetic or natural, inorganic or organic substance which is incorporated in agricultural and horticultural fungicides to assist their active ingredients to reach locations to be treated therewith and to facilitate the storage, transportation and handling of such active ingredients.

As solid carriers suitable for use in the practice of this invention, may be mentioned clays such as montmorillonite and kaolin, inorganic materials such as diatomaceous earth, terra abla, talc, vermiculite, gypsum, calcium carbonate, silica gel, ammonium sulfate and the like, vegetable-or plant-origin organic materials such as soybean flour, saw dust, wheat flour ant the like, urea, etc.

Among suitable liquid carriers, may be included aromatic hydrocarbons such as benzene, toluene, xylene, cumene, etc., paraffinic hydrocarbons such as kerosine, mineral oil and the like, halogenated hydrocarbons such as carbon tetrachloride, chloroform, dichloroethane and the like, ketones such as acetone, methyl ethyl ketone, etc., ethers such as dioxane, tetrahydrofuran and the like, alcohols such as methanol, propanol, ethylene glycol and the like, dimethyl formamide, dimethylsulfoxide, glycerin, water, etc.

In order to enhance the effectiveness of the compounds according to this invention, it is possible to use such adjuvants as given below either singly or in combination in accordance with the purpose of each application thereof while taking the types of their preparation forms and their application fields.

Namely, exemplary adjuvants may include anionic surfactants such as alkyl sulfates, aryl sulfonates, succinates, polyethylene glycol alkyl aryl ether sulfates, and the like, cationic surfactants such as alkylamines, polyoxyethylene alkylamines etc., non-ionic surfactants such as polyoxyethylene glycol ethers, polyoxyethylene glycol esters, polyol esters and the like, and amphoteric surfactants.

Besides, may be mentioned as stabilizers, stickeners, lubricants and the like isopropyl hydrogenphosphate, calcium stearate, wax, casein lime, sodium alginate, methylcellulose, carboxymethylcellulose, gum arabi, etc. However, it should be borne in mind that these ingredients are not limited to the above-recited specific examples.

When using the compounds of this invention as fungicides, they may be applied simultaneously with or as mixtures with other agricultural chemicals such as insecticides, other fungicides, acaricides, nematocides, viricides, herbicides, plant growth regulators,and attractants, for example, organophosphate-base compounds, carbamate-type compounds, dithiocarbamate-type compounds, thiolcarbamate-type compounds, organic chlorine compounds, dinitro compounds, antibiotics, urea-base compounds, triazine-type compounds, fertilizers, etc.

A variety of preparations containing the above-described active ingredients according to this invention, namely applicable compositions containing such active ingredients may be used in accordance with application methods commonly adopted in the agricultural fields, more specifically, by applying them over the surfaces of fields, plants or the like (e.g., spraying them as liquid compositions, misting, atomizing, dusting, granular application, applying them onto the surface of irrigated water); fumigation and soil application (for example, mixing, fumigation, application together with irrigation); surface application (for example, coating, powdering, and covering); dipping; and the like application methods.

The amount of application may vary depending on each application purpose. It is however preferred to apply 0.1-10 kg per hectare in terms of an active ingredient.

Certain examples of preparations of agricultural and horticultural fungicides containing the compounds according to this invention as active ingredients will be described below. Needless to say, the present invention is not limited to use of the additives, their proportions and contents of active ingredients which will follow. Compounds of this invention, which will be used as active ingredients, will be expressed in terms of the compound number given in Table 1. All designations of "parts" will mean "parts by weight".

Preparation Example 1: Wettable Powder

Wettable powder, which contained 30% of Compound No. 1 as an active ingredient, was prepared by milling 300 parts of Compound No. 1, 440 parts of diatomaceous earth, 200 parts of terra abla, 25 parts of sodium ligninsulfonate, 15 parts of sodium alkylbenzenesulfonate, and 20 parts of polyoxyethylene nonyl phenyl ether into an intimate mixture.

Preparation Example 2: Emulsifiable Concentrate

An emulsifiable concentrate, which contained 30% of Compound No. 6 as an active ingredient, was prepared by dissolving with mixing 300 parts of Compound No. 16, 100 parts of cyclohexanone, 400 parts of xylene and 200 parts of "Sorpol" (a surfactant produced by Toho Kagaku K.K.) into a uniform solution.

Preparation Example 3: Dust

Dust, which contained 2% of Compound No. 2 as an active ingredient, was prepared by milling 20 parts of Compound No. 2, 5 parts of calcium stearate, 5 parts of powdery silica gel, 200 parts of diatomaceous earth, 300 parts of terra abla, and 470 parts of talc into an intimate powdery mixture.

Preparation Example 4: Oil Solution

An oil solution, which containing 10% of Compound No. 2 as an active ingredient, was prepared by dissolving with stirring 10 parts of Compound No. 2 in 90 parts of ethyl cellosolve.

Next, the effects of the compounds according to this invention as fungicides will be described in the following Tests. Sample compounds will be expressed in terms of the compound numbers given in Table 1.

Test 1: Alternaria Leaf Spot (*Alternaria mali*) Control Test

Apple plants (specie: Star King; 2 year-old) having about 8 newly-developed leaves, which were individually potted in No. 3 unglazed pots, were sprayed to the point of 100 ml per 3 pots with a chemical formulation of a predetermined concentration (each sample compound was prepared into wettable powder in accordance with the procedure of Preparation Example 1 and then diluted to the predetermined concentration with water), using a spray gun (1.0 kg/cm²). After the plants were dried in air, they were sprayed and inoculated with a spore suspension of *Alternaria mali* which had in advance been cultivated for 7 days in a culture medium of "V-8" vegetable juice. The plants were incubated for 3 days at 23°-25° C. and at a relative humidity of 95% or higher.

The number of lesions was counted with respect to each of the 8 leaves in each pot. The average lesion number per leaf was then calculated, on which was determined control value in accordance with the following equation.

$$\text{Control value} = \left(1 - \frac{\text{Average lesion number in treated section}}{\text{Average lesion number in untreated section}}\right) \times 100$$

Results are shown in Table 2. Methyl thiophanate, having a structural formula

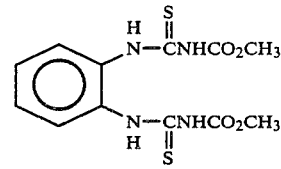

and used as control, is a chemical commonly employed as a chemical for controlling Alternaria leaf spot (*Alternaria mali*).

TABLE 2

| Sample Compound Number | Concentration of Active Ingredient (ppm) | Control Value (%) | Phytotoxicity |
|---|---|---|---|
| 1 | 250 | 100 | none |
| 2 | 250 | 100 | none |
| 8 | 250 | 83 | none |
| 12 | 250 | 95 | none |
| 13 | 250 | 95 | none |
| 14 | 250 | 100 | none |
| 17 | 250 | 100 | none |
| 20 | 250 | 92 | none |
| 24 | 250 | 83 | none |
| 25 | 250 | 80 | none |
| 28 | 250 | 80 | none |
| 45 | 250 | 85 | none |
| 46 | 250 | 85 | none |
| Compound A* | 250 | 79 | none |

*Compound A: Methyl thiophanate.

Test 2: Potato Late Blight (*Phytophthora infestans*) Control Test (Preventive Effects)

Potato plants (specie: Danshaku; about 25 cm tall), which were individually cultivated in pots in a greenhouse, were sprayed to the point of 50 ml per 3 pots with a chemical formulation of a predetermined concentration (each sample compound was prepared into wettable powder in accordance with the procedure of Preparation Example 1 and then diluted with water to the predetermined concentration), using a spray gun. The plants were then dried in air. A zoosporangial suspension was prepared using *Phytophthora infestans* which had in advance been cultivated for 7 days on potato pieces. The zoosporangial suspension was then treated at 7° C. for further 3 hours, thereby preparing a zoospore suspension. The potato plants, which had been sprayed with the chemical formulation, were sprayed and inoculated with the zoospore suspension. The sample plants were incubated for 6 days at temperatures of 17°-19° C. and relative humidity of 95% or higher. Thereafter, the extent of lesion development was investigated. The following rank reading was employed:

| Lesion Index | Percent Leaf Area Infected |
| --- | --- |
| 0 | 0% |
| 1 | 1–5% |
| 2 | 6–25% |
| 3 | 26–50% |
| 4 | 51% and up |

Lesion index was calculated for each leaf in accordance with the above rank reading and the thus-obtained average infection degrees are given in Table 3. Zineb having the structural formula

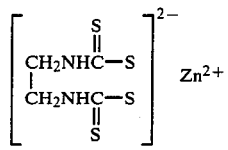

and tetrachloroisophthalonitrile are both commercially sold and generally used as agents for controlling Potato late blight (*Phyrophthora infestans*). 5-n-Butyl-2-(N,N-dimethyl)amino-4-hydroxy-6-methylpyrimidine is discloses as a fungicide in British Patent Specification No. 1,182,584. These known compounds were used as control compounds.

TABLE 3

| Sample Compound Number | Concentration of Active Ingredient (ppm) | Lesion Index | Phytotoxicity |
| --- | --- | --- | --- |
| 1 | 500 | 0 | none |
| 2 | 500 | 0 | none |
| 3 | 500 | 0.70 | none |
| 4 | 500 | 0 | none |
| 8 | 500 | 0.47 | none |
| 9 | 500 | 0 | none |
| 10 | 500 | 0.30 | none |
| 12 | 500 | 0 | none |
| 13 | 500 | 0.05 | none |
| 15 | 500 | 0.85 | none |
| 16 | 500 | 0 | none |
| 17 | 500 | 0 | none |
| 18 | 500 | 0.85 | none |
| 19 | 500 | 0.30 | none |
| 21 | 500 | 0.37 | none |
| 22 | 500 | 0 | none |
| 24 | 500 | 0.55 | none |
| 37 | 500 | 0.80 | none |
| 38 | 500 | 0.62 | none |
| 40 | 500 | 0 | none |
| 41 | 500 | 0 | none |
| 42 | 500 | 0.58 | none |
| 44 | 500 | 0.29 | none |
| 45 | 500 | 0.10 | none |
| Compound B* | 500 | 1.04 | none |
| Compound C* | 500 | 1.25 | none |
| Compound D* | 500 | 3.50 | none |
| Untreated | — | 3.85 | — |

*Compound B: Zinc ethylene-bis(dithiocarbamate);
Compound C: Tetrachloroisophthalonitrile; and
Compound D: 5-n-Butyl-2-(N,N—dimethyl)amino-4-hydroxy-6-methylpyrimidine Test 3: Potato Late Blight (*Phytophthora infestans*) Control Test (Curative Effects)

A zoospore suspension of potato late blight prepared in the same manner as in Test 2 was sprayed and inoculated to potato plants similar to those employed in Test 2. After inoculating the potato plants for 20 hours at temperatures of 17°–19° C. and humidity of 95% or higher, the potato plants were sprayed by a chemical preparation of a predetermined concentration (each sample compound was prepared into wettable powder following the procedure of Preparation Example 1 and then diluted with water to the predetermined concentration) to the point of 50 ml per 3 pots using a spray gun (1.0 kg/cm$^2$). After they were dried in air, they were kept for 5 days again at temperatures of 17°–19° C. and humidity of 95% or higher. Thereafter, the extent of development of lesions was investigated.

The same rank reading as that used in Test 2 was used. Similar to Test 2, lesion index was determined for each leaf and the thus-obtained average infection degrees are shown in Table 4.

TABLE 4

| Sample Compound Number | Concentration of Active Ingredient (ppm) | Lesion Index | Phytotoxicity |
| --- | --- | --- | --- |
| 1 | 500 | 0 | none |
| 2 | 500 | 0 | none |
| 3 | 500 | 0.85 | none |
| 4 | 500 | 0.12 | none |
| 8 | 500 | 0.30 | none |
| 9 | 500 | 0 | none |
| 12 | 500 | 0.30 | none |
| 13 | 500 | 0.10 | none |
| 15 | 500 | 0.96 | none |
| 16 | 500 | 0 | none |
| 17 | 500 | 0 | none |
| 21 | 500 | 0.30 | none |
| 22 | 500 | 0 | none |
| 40 | 500 | 0 | none |
| 41 | 500 | 0 | none |
| 45 | 500 | 0.15 | none |
| Compound B* | 500 | 3.45 | none |
| Compound C* | 500 | 3.29 | none |
| Compound D* | 500 | 3.75 | none |
| Untreated | — | 3.50 | — |

*Compound B: Zinc ethylene-bis(dithiocarbamate);
Compound C: Tetrachloroisophthalonitrile; and
Compound D: 5-n-Butyl-2-(N,N—dimethyl)aino-4-hydroxy-6-methylpyrimidine Test 4: Cucumber Downy Mildew (*Pseudoperonospora cubensis*) Control Test (Preventive Effects)

Cucumber plants (specie: Sagami-Hanjiro; in the two foliage leaves stage), which had been cultivated individually in pots in a green house, were sprayed to the point of 30 ml per 3 pots with a chemical formulation of a predetermined concentration (prepared by converting each sample compound into wettable powder in the same manner as in Preparation Example 1 and then diluting the wettable powder with water to the predetermined concentration), using a spray gun (1.0 kg/cm$^2$), and then dried in air. Spore of *Pseudoperonospora cubensis* was collected from infected areas of cucumber leaves which had been infected by downy mildew. Using the thus-collected spore of *Pseudoperonospora cubensis* and deionized water, a spore suspension was prepared. The spore suspension was sprayed and inoculated onto the abaxial surface of each leaf. The thus-inoculated cucumber plants were immediately incubated at temperatures of 18°–20° C. and humidity of 95% or higher for 24 hours and then transferred into a green house (temperature: 18° C.–27° C.). After an elapsed time of 7 days, the extent of development of lesions was investigated.

The same rank reading as used in Test 2 was also used in the present test. Similar to Test 2, lesion index was determined for each leaf and the thus-obtained average lesion indexes are shown in Table 5. Incidentally, the control compounds, zineb and tetrachloroisophthalonitrile are chemicals commercially available and commonly employed as fungicides for controlling cucumber downy mildew (*Pseudoperonospora cubensis*). On the other hand, the other control compound, 5-n-butyl-2-(N,N-dimethyl)amino-4-hydroxy-6-methylpyrimidine, is a compound disclosed as a fungicide in British Patent Specification No. 1,182,584.

TABLE 5

| Sample Compound Number | Concentration of Active Ingredient (ppm) | Lesion Index | Phytotoxicity |
| --- | --- | --- | --- |
| 1 | 500 | 0 | none |
| 2 | 500 | 0 | none |
| 4 | 500 | 0 | none |
| 6 | 500 | 0.07 | none |
| 8 | 500 | 0.20 | none |
| 11 | 500 | 0.05 | none |
| 12 | 500 | 0 | none |
| 15 | 500 | 0.47 | none |
| 16 | 500 | 0 | none |
| 21 | 500 | 0.18 | none |
| 22 | 500 | 0 | none |
| 24 | 500 | 0.10 | none |
| 25 | 500 | 0.18 | none |
| 29 | 500 | 0.25 | none |
| 30 | 500 | 0.20 | none |
| 39 | 500 | 0 | none |
| 40 | 500 | 0.03 | none |
| 41 | 500 | 0 | none |
| Compound B* | 500 | 1.85 | none |
| Compound C* | 500 | 1.52 | none |
| Compound D* | 500 | 3.80 | none |
| Untreated | — | 4.00 | — |

*Compound B: Zinc ethylene-bis(dithiocarbamate);
Compound C: Tetrachloroisophthalonitrile; and
Compound D: 5-n-Butyl-2-(N,N—dimethyl)amino-4-hydroxy-6-methylpyrimidine Test 5: Cucumber Downy Mildew (*Pseudoperonospora cubensis*) Control Test (Curative Effects)

A suspension of the spore of *Pseudoperonospora cubensis*, which had been prepared in the same manner as in Test 4, was sprayed and inoculated to cucumber plants similar to those employed in Test 4. The cucumber plants were incubated for 24 hours at temperatures of 18°–20° C. and humidity of 95% or higher. The cucumber plants were then sprayed to the point of 30 ml per 3 pots with a chemical formulation of a predetermined concentration (which was obtained by preparing each sample compound into wettable powder by the same method as employed in Preparation Example 1 and diluting same to the predetermined concentration with water), using a spray gun (1.0 kg/cm²). They were then transferred into a green house (temperature: 18°–27° C.) and, after an elapsed time of 7 days, the extent of development of lesions was investigated.

Investigation results were analyzed following the same rank reading as that employed in Test 2. In the present test, in lesion index was also determined for each leaf and the thus-obtained average lesion indexes are shown in Table 6.

TABLE 6

| Sample Compound Number | Concentration of Active Ingredient (ppm) | Lesion Index | Phytotoxicity |
| --- | --- | --- | --- |
| 1 | 500 | 0 | none |
| 2 | 500 | 0 | none |
| 4 | 500 | 0 | none |
| 6 | 500 | 0 | none |
| 11 | 500 | 0.05 | none |
| 12 | 500 | 0 | none |
| 16 | 500 | 0 | none |
| 21 | 500 | 0.20 | none |
| 22 | 500 | 0 | none |
| 24 | 500 | 0.07 | none |

TABLE 6-continued

| Sample Compound Number | Concentration of Active Ingredient (ppm) | Lesion Index | Phytotoxicity |
| --- | --- | --- | --- |
| 25 | 500 | 0.12 | none |
| 29 | 500 | 0.20 | none |
| 30 | 500 | 0.07 | none |
| 39 | 500 | 0.07 | none |
| 40 | 500 | 0.05 | none |
| 41 | 500 | 0.10 | none |
| 45 | 500 | 0.10 | none |
| Compound B* | 500 | 4.00 | none |
| Compound C* | 500 | 4.00 | none |
| Compound D* | 500 | 4.00 | none |
| Untreated | — | 4.00 | — |

*Compound B: Zinc ethylene-bis(dithiocarbamate);
Compound C: Tetrachloroisophthalonitrile; and
Compound D: 5-n-Butyl-2-(N,N—dimethyl)amino-4-hydroxy-6-methylpyrimidine

We claim:

1. A 5-methylthiopyrimidine derivative represented by the following formula (I):

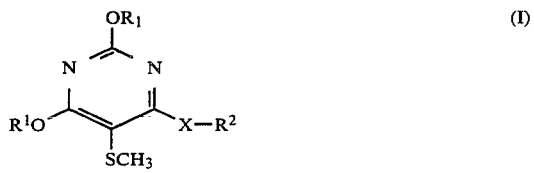

wherein $R^1$ means an alkyl group having 1–6 carbon atoms or a phenyl, benzyl, alkenyl or alkoxyalkyl group, $R^2$ denotes an alkyl group having 1–6 carbon atoms, a phenyl, halogen-substituted phenyl, alkenyl, ω-phenyl-substituted alkenyl, alkynyl, alkoxyalkyl, alkoxyalkoxyalkyl, alkylthioalkyl, aminoalkyl, alkoxycarbonylalkyl, aminocarbonylalkyl, furfuryl, thienylmethyl or tetrahydrofuryl group or a

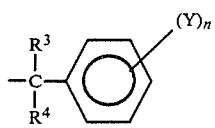

in which $R^3$ and $R^4$ are individually a hydrogen atom or methyl group, Y means a hydrogen or halogen atom or a methyl or methoxy group, and n stands for an integer of 1 or 2, and X denotes an oxygen or sulfur atom.

2. A 5-methylthiopyrimidine derivative according to claim 1, wherein $R^1$ is a methyl group.

3. A 5-methylthiopyrimidine derivative according to claim 2, wherein $R^1$ is a methyl group and $R^2$ is also a methyl group.

4. A 5-methylthiopyrimidine derivative represented by the following formula (I):

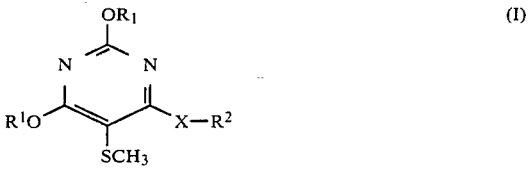

wherein $R^1$ is a methyl group, $R^2$ is a propargyl or allyl group, and X is an oxygen atom.

5. An agricultural and horticultural fungicidal composition comprising, a carrier and/or an adjuvant and, as an active ingredient, a fungicidally effective amount of a 5-methylthiopyrimidine derivative represented by the following formula (I):

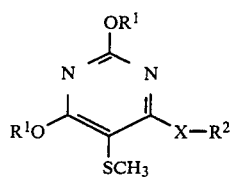  (I)

wherein $R^1$ means an alkyl group having 1–6 carbon atoms or a phenyl, benzyl, alkenyl or alkoxyalkyl group, $R^2$ denotes an alkyl group having 1–6 carbon atoms, a phenyl, halogen-substituted phenyl, alkenyl, ω-phenyl-substituted alkenyl, alkynyl, alkoxyalkyl, alkoxyalkoxyalkyl, alkylthioalkyl, aminoalkyl, alkoxycarbonylalkyl, aminocarbonylalkyl, furfuryl, thienylmethyl or tetrahydrofuryl group of a

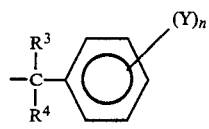

in which $R^3$ and $R^4$ are individually a hydrogen atom or methyl group, Y means a hydrogen or halogen atom or a methyl or methoxy group, and n stands for an integer of 1 or 2, and X denotes an oxygen or sulfur atom.

6. A method for controlling plant diseases, which method comprises applying to plant pathogens or their habitats, as an effective component, 0.1–10 kg per hectare of a 5-methylthiopyrimidine derivative represented by the following formula (I):

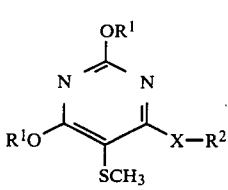  (I)

wherein $R^1$ means an alkyl group having 1–6 carbon atoms or a phenyl, benzyl, alkenyl or alkoxyalkyl group, $R^2$ denotes an alkyl group having 1–6 carbon atoms, a phenyl, halogen-substituted phenyl, alkenyl, ω-phenyl-substituted alkenyl, alkynyl, alkoxyalkyl, alkoxyalkoxyalkyl, alkylthioalkyl, aminoalkyl, alkoxycarbonylalkyl, aminocarbonylalkyl, furfuryl, thienylmethyl or tetrahydrofuryl group or a

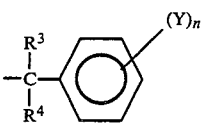

in which $R^3$ and $R^4$ are individually a hydrogen atom or methyl group, Y means a hydrogen or halogen atom or a methyl or methoxy group, and n stands for an integer of 1 or 2, and X denotes an oxygen or sulfur atom.

* * * * *